US010188852B2

United States Patent
Pinna

(10) Patent No.: US 10,188,852 B2
(45) Date of Patent: Jan. 29, 2019

(54) PATCH ABLE TO PRODUCE MICROCURRENTS

(71) Applicant: FASTMEDITALIA S.R.L., Desio (Monza Brianza) (IT)

(72) Inventor: Marco Pinna, Desio (IT)

(73) Assignee: FASTMEDITALIA S.R.L., Desio (Monza) (IT)

( * ) Notice: Subject to any disclaimer, the term of this patent is extended or adjusted under 35 U.S.C. 154(b) by 0 days.

(21) Appl. No.: 15/508,942

(22) PCT Filed: Jul. 27, 2015

(86) PCT No.: PCT/IB2015/055662
§ 371 (c)(1),
(2) Date: Mar. 6, 2017

(87) PCT Pub. No.: WO2016/038477
PCT Pub. Date: Mar. 17, 2016

(65) Prior Publication Data
US 2017/0232249 A1 Aug. 17, 2017

(30) Foreign Application Priority Data
Sep. 8, 2014 (IT) .............. VA2014A0025

(51) Int. Cl.
*A61N 1/00* (2006.01)
*A61N 1/04* (2006.01)
*A61N 1/30* (2006.01)

(52) U.S. Cl.
CPC ........... *A61N 1/0492* (2013.01); *A61N 1/044* (2013.01); *A61N 1/0428* (2013.01); *A61N 1/0436* (2013.01); *A61N 1/0448* (2013.01); *A61N 1/0456* (2013.01); *A61N 1/30* (2013.01)

(58) Field of Classification Search
CPC .. A61N 1/0436; A61N 1/0448; A61N 1/0456; A61N 1/0492; A61N 1/0428; A61N 1/044; A61N 1/30
See application file for complete search history.

(56) References Cited

U.S. PATENT DOCUMENTS

| 2005/0010161 A1 | 1/2005 | Sun et al. | |
|---|---|---|---|
| 2005/0085751 A1* | 4/2005 | Daskal | A61N 1/0436 602/2 |
| 2011/0118655 A1 | 5/2011 | Fassih et al. | |
| 2011/0208111 A1* | 8/2011 | Henley | A61N 1/044 604/20 |

FOREIGN PATENT DOCUMENTS

| DE | 10 2008 036 101 A1 | 2/2010 |
|---|---|---|
| EP | 2 618 411 A1 | 7/2013 |
| KR | 10-2013-0026647 A | 3/2013 |

\* cited by examiner

Primary Examiner — George Manuel
(74) Attorney, Agent, or Firm — Vorys, Sater, Seymour & Pease LLP

(57) ABSTRACT

Provided is a patch able to produce micro-current to be applied on human skin including a support for electrodes spaced from each other and apt to create voltages typical of galvanic piles, connection means between the electrodes, an adhesive layer applied on one side of the support and apt to adhere to the skin and a protection liner applied on the adhesive layer, the support being a membrane permeable to the moisture inside the electrodes, and the connection means being defined by a material that is avid of moisture, such as silica impregnating the membrane.

10 Claims, 1 Drawing Sheet

PATCH ABLE TO PRODUCE MICROCURRENTS

Figure 1:
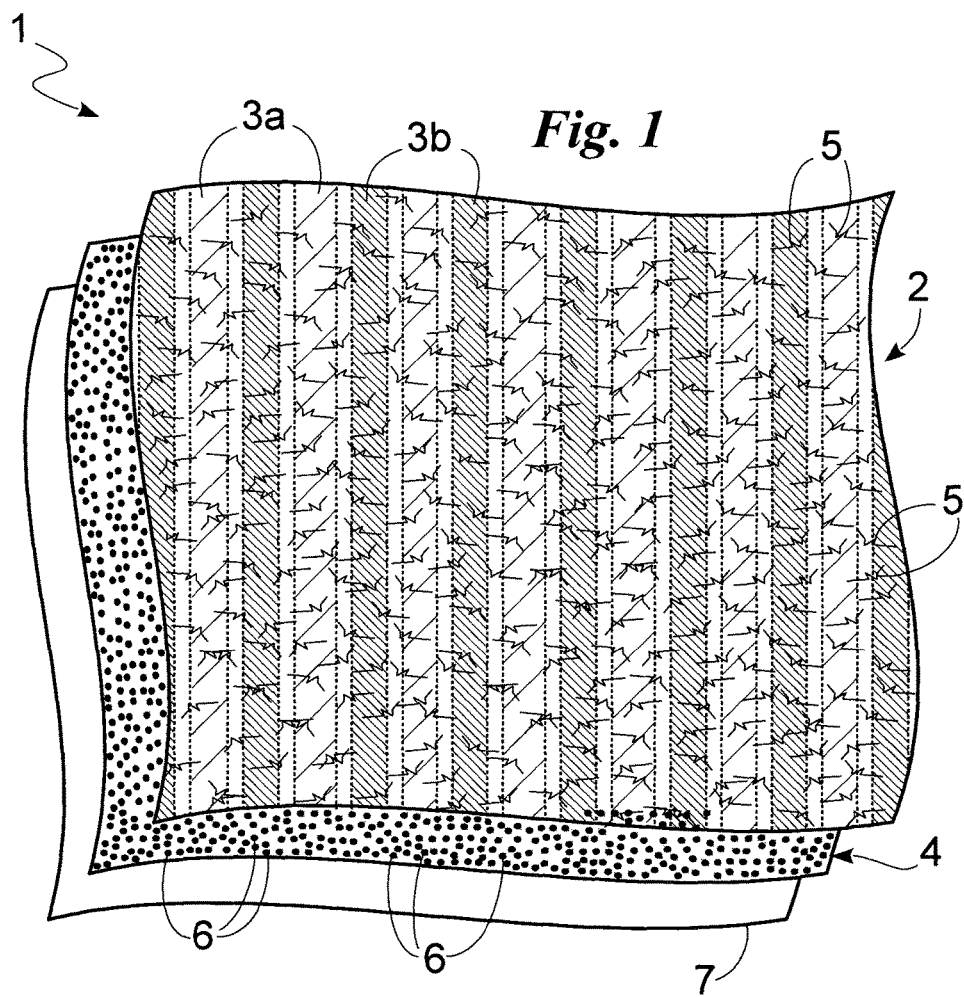

The invention relates to a patch to be applied on human skin for cosmetic and medical purposes, including copper filaments and silver or zinc filaments, in order to create voltages typical of galvanic piles and capable of producing electrostimulation through electrical microcurrents, as specified in the preamble of the first Claim.

Microcurrents are known to be used in electrostimulation both with DC current and AC current.

Today, in hospital, medical and healthcare environments, a wide range of electrical stimulators are available, that offer a broad range of different parameters, such as frequency, type of wave, pulse width, rest time and so on.

This has contributed to the diffusion of a therapy called transcutaneous electrical nerve stimulation (TENS).

Microcurrent electrical neuromuscular stimulation (MCR) was developed quite recently and is increasingly being used for its advantages.

Unlike the currents normally used for conventional electrostimulations, that use currents in the order of milliamperes (mA), the microcurrent uses intensities in the order of microamperes (µA).

These current intensities are not perceived by humans and therefore do not create an unpleasant, annoying, and sometimes painful "shock" effect and offer a series of advantages: safety, comfort, decrease of acute and chronic pain, a faster tissue recovery and quick healing of wounds. They also stimulate the production of collagen that promotes skin elasticity.

However, the devices currently used for the microcurrent therapy (MRC) have a number of long-term complications that discourage their use.

They are most often impractical and expensive, because they are equipped with conventional sources of energy, such as batteries and plugs that need to be connected to the power network.

The fabrics with copper and zinc filaments on the market generally have these filaments intertwined with each other, hindering the widespread and constant production of microcurrents, because the intertwined filaments very often touch one another creating short circuits.

Besides, their application is made manually through devices that need to be passed on the area to be treated and applied with strings and laces.

They do not allow a normal activity of work and study.

Besides, said devices are one-sized and it is not possible to change their area of application and therapeutic range easily.

Some patches present on the market for cosmetic use offer the capacity to generate microcurrents, but are equipped with a single galvanic cell, thus with a limited and concentrated range of action and the systems used for their production are very expensive.

Among the relevant patents, we wish to highlight the patents US 2005/010161 A1 and US 2011/118655 A1.

The patent US 2005/010161 A1, published on Jan. 13, 2005 entitled "Method of treating acne and rosacea with galvanic generated electricity", describes a complex structure where electrodes of large dimensions are placed on one side of an isolating layer and joined on the opposite side of the isolating layer by an electric connection crossing the layer.

An adhesive strip containing active agents is arranged under the electrodes, and is applied on the patient.

In other executions, the electrodes and their electrical connection are placed at or within the adhesive layer.

This is a complex and cumbersome appliance that may also include a switch, in correspondence with the electrical connection, to prevent the flow of current between the electrodes.

The patent US 2011/118655 A1, published on May 19, 2011 and entitled "Galvanic skin treatment device", relates to a structure with a great number of sections on pieces of electrodes and is arranged on a side of a support or substrate.

Each couple of electrode sections is joined electrically by a bridge connector, applied on the same side of the substrate where said sections are arranged.

This structure is very delicate and complex to make.

In the above mentioned patents, the use of specific bridges or electric connections between the electrodes complicates the structure and exposes it to the risk of malfunctioning in case of rupture of these bridges.

Besides, the electrodes, and in some cases the same bridges, require at least one additional layer that increases the complexity of the structures and their rigidity.

Since the galvanic pile, in a functional sense, underlies the present invention and the devices generating microcurrents, patent EP 2618411 A1, published on Jun. 24, 2013, entitled "Thin battery electrode group, thin battery, and electronic device" has been highlighted as well.

This patent relates to an improvement of the galvanic pile, which allows producing a very thin battery, defined by the various thin layers superposed on one another as a pack.

The battery is complex, it is designed for electronic devices and has a great number of layers in the examples because the electrodes are sheets in an overlapped position as for the galvanic pile.

In this situation, the technical task at the base of the present invention is to provide a patch capable of producing microcurrents that can overcome the aforementioned drawbacks.

The technical task is achieved by a patch capable of producing microcurrents and consequently micro magnetic fields according to the independent claims.

Preferred embodiments are highlighted in the independent claims.

Figure 2:
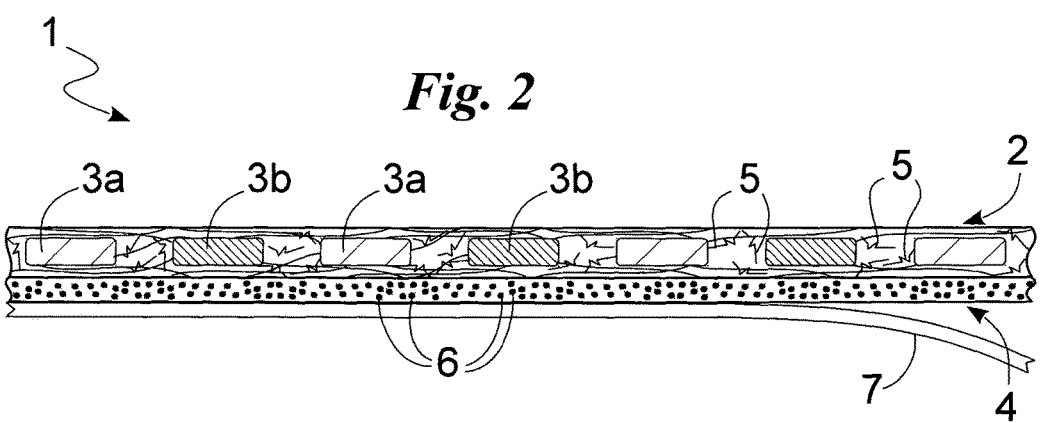

The characteristics and advantages of the invention are explained below in the detailed description of preferred embodiments of the invention, with reference to the accompanying drawings, in which:

FIG. 1 shows a view of a portion of a patch according to the invention in its different layers; and FIG. 2 shows, in sectional view and an enlarged scale, the portion of patch of the previous figure.

With reference to the Figures, the patch according to the invention is globally indicated with number 1.

The patch is applied on human skin for cosmetic or medical purposes and comprises a support defined by a moisture-permeable membrane 2 defined, for example, by a preferably fibrous fabric, in which the electrodes 3a, 3b are inserted spaced from each other, to create voltages typical of the galvanic piles and potentially capable of producing micro-electrical currents.

Electrodes 3a, 3b can be chosen in a wide range of materials and are, preferably, copper filaments and zinc filaments.

An adhesive layer 4 covers a side of the membrane 2 or moisture-permeable fabric.

Membrane 2 presents connection means 5 inside between electrodes 3a, 3b. These connection means 5 are chosen in order to not substantially make an electric communication bridge when patch 1 is not used, but such as to make it when patch 1 is applied to the skin.

The means of connection 5 are indeed defined by a material that is avid of moisture and compatible with dermal application, that impregnates the permeable membrane.

In particular, the material avid of moisture and compatible with dermal application is a material commonly called "colloidal silica" or "gel of silica" or "silica gel", consisting of a polymer of silicon dioxide $(SiO_2)_n$.

Silica, or an equivalent material—once in contact with the skin by means of the adhesive—captures the sweat fluid molecules, typically made of salt and water, allowing the ion exchange between the copper filaments and the zinc filaments. Sweat is a slightly acid hypotonic fluid secreted by the skin sweat glands and consists of water and, among other substances, bipolar ions: Na+, K+, Cl−. It should be emphasised that patch 1, once applied to the skin, causes an occlusive effect forcing the pores to release $H_2O$ containing physiological salts and sodium, potassium and chlorine ions, thus determining a humidification of the glue and fabric.

The couples of copper filaments and zinc filaments 3a, 3b, or electrodes in general, being in an acid hydrosaline environment and with free ions, generate an electric current of a few dozens of microamperes and a micro-magnetic field of a few nanotesla.

The action of microcurrents and micro-electromagnetic fields allows to activate the electric charges in the tissues (good conductors) and in the micro blood vessels. This induces the formation of microcurrents that, at the level of biological membranes, favour the ion exchange, the use of oxygen and the restoration of the membrane potential (determining an increase of the excitability threshold) thus obtaining a high analgesic effect (TENS effect).

By placing in the adhesive layer 4 substances 6 with a cosmetic, medical or pharmaceutical activity whose molecules have polar or bipolar characteristics, the microcurrents allow the ions of these molecules to follow the direction of the electric charge with which they are provided, thereby considerably facilitating the dermal barrier passage.

As known, polar molecules, also called bipolar molecules, differ from non-polar ones in that they present a partial positive charge on a part of the molecules and a partial negative charge on another part.

More in detail, patch 1 according to the invention is preferably a shaped element in fabric 2 at least partially impregnated with silica (that means as said, colloidal silica $(SiO_2)_n$ or silica gel) and containing filaments of copper and zinc 3a, 3b parallel to each another and spaced at least 0.5 millimeters from each other.

Preferably, a distance is provided between the filaments of copper and those of zinc 3a, 3b between 1.5 and 2.5 millimeters.

Said filaments have a width—in parallel to fabric 2—of at least 0.3 mm and have each, preferably, a width between 1.5 and 2.5 millimeters.

The surface of the fabric 2 is at least partially coated on one side with an adhesive layer 4 made of a layer of an adhesive polymer containing electrolytes compatible with the human dermis.

Electrolytes are able to act as accelerators of the ions generated by the microcurrents.

Then a patch 1 is formed able to stick onto the skin in order to enable the microcurrents developed from the copper and zinc poles to penetrate the skin and physiologically excite the cellular interstices and facilitate the passage of any active substances polarised through the dermis.

Even more in detail, the membrane 2, that is impregnated, is made of a soft fabric of about 100 grams per square meter preferably in polyester or cotton, loaded with silica for at least 10 grams per square meter, preferably between 15 and 25 grams per square meter.

The weight of the copper and zinc filaments 3a, 3b is chosen equal to at least 20 grams per square meter for copper and 20 grams per square meter for zinc, preferably between 35 and 45 grams per square meter for each of the two filaments.

The material of the adhesive layer 4 is arranged to present characteristics of permeability to the molecules of the hydrosaline liquid and to contain electrolytes and polar or bipolar substances inside.

Preferably, it is an acrylic or polyurethane adhesive with a weight from 10 to 100 grams per square meter, preferably from 30 to 70 grams per square meter.

A terminal layer or protective lamina referred to as "liner" 7 protects the adhesive layer 4 and allows its handling.

This layer, lamina, or liner 7 is preferably made of polyester, silicone paper, coated paper, of 15 to 200 grams per square meter.

In the adhesive layer 4, the pharmaceutical, cosmetic or medical substances 6 can be defined by natural substances such as Arnica, by cosmetic substances such as hyaluronic acid or active pharmaceutical substances such as Diclofenac sodium.

These substances are in contact with fabric 2 and with the dermis thanks to the adhesive 4 while exercising their activity.

Patch 1 of the present invention is preferably made as follows.

A fabric 2 is prepared presenting copper filaments spaced from those of zinc and parallel to the latter, in a similar way as in a galvanic pile.

In particular, a fabric 2 is arranged with longitudinally alternated strips of copper and zinc filaments 3a, 3b, or other material, all with a width of about 2 mm and spaced from each another of about 1 mm by fibres of this fabric 2.

In order to obtain that the said fabric fibres, once applied onto to skin, are able to act as a semiconductor, they are wetted by a solution containing silica.

Silica, when in contact with the skin, absorbs the typical slightly acid human sweat moisture, and allows the ion exchanges in the fabric, which are needed to transmit the microcurrents.

The coil of fabric obtained is then coated with an adhesive agent which can adhere to the skin and protected by a PET or paper siliconized liner 7.

The coil obtained is cut into smaller coils and die-cut into the desired shape with a die-cutting machine.

After the desired patch 1 is obtained, it was verified whether the copper and zinc filaments 3a, 3b spaced from each other in the fabric 2 loaded with silica are able, in the conditions of use, to generate microcurrents and also at what intensity.

To assess the capacity of generating microcurrents, a simulation of what happens once the patch is applied onto the skin was performed.

A slightly acid solution (with pH 6.3) was vaporized, considering that human sweat generally has a pH between pH 4 and pH 6.5.

The vaporisation was calibrated keeping in mind that, as mentioned, the patch has an occlusive effect once applied to the skin, forcing the pores to release $H_2O$ containing the physiological salts and sodium, potassium and chlorine ions determining a humidification of the glue and fabric.

By this, the humidification works as a dielectric means allowing the passage of the ions between the filaments of copper and zinc.

The microcurrent is then generated spontaneously thanks to the potential electronegative difference, that is as follows (in Volts): Copper 1.90 Zinc 1.65 Volts, for a potential difference)(ΔE °) of 250 mV.

To verify the intensity (in μA) of the microcurrents a particular instrument was used in order to measure currents at low intensity, a precision HAMEG INSTRUMENTS HM8112 multimeter, equipped with a probe able to engage two +/− electrodes.

The results in five points of the patch (centre, upper, lower, left, right) were as follows:

Point 1 (in the middle): 90 mV-340 μA
Point 2 (upper): 85 mV-290 μA
Point 3 (lower): 90 mV-350 μA
Point 4 (left): 95 mV-380 μA
Point 5 (right): 90 mV-340 μA By assessing the measurements carried out, it can be concluded that the average intensity of the microcurrents generated by the dampened patch 1 simulating the body application is about 340 μA.

The intensity of the microcurrent measured is absolutely in line with the therapeutic purposes to be achieved by patch 1 and shows that there are constant values on the various points, which are useful for a correct application.

In order to further clarify the nature, shape, structure and method of production of patch 1, some examples of embodiments shall be given.

EXAMPLE 1

Example 1 refers to the preparation of a patch 1 according to the invention for the treatment of osteo-articular pain.

In a container equipped with a propeller stirrer 45 kg of solvent acrylic adhesive (for example the Duro-tak 2353 adhesive by National Starch & Chemical) are introduced cold, the adhesive allowing an excellent breathability and an excellent capacity—once reduced in films—of incorporating water-soluble molecules.

500 gr of Sodium Chloride, are also introduced, diluted in $H_2O$ in a 1/1 proportion (obtained by stirring with the specific stirrer for 5 minutes).

Then it is mixed at low speed for 10 minutes (120 rev/min) with the propeller stirrer until a uniform mass compound is obtained.

Using a coating machine and a compressed air pump, the acrylic adhesive compound is transferred on a rotating cylinder doctor blade, having adjusted the doctor blade thickness to about 150 microns.

The doctor blade spreads the adhesive (for the set thickness) onto a continuous foil or liner in plastic material, for example 100-micron polyester.

The adhesive spread on the liner goes, at a speed of 8 meters per minute, through four oven stations, the first oven having a temperature set at 40° C., the second one at 50° C., the third one at 70° C. and the fourth one at 100° C.

When coming out of the ovens, the adhesive layer is completely free from solvents, which have evaporated in the oven stations.

The thickness of the adhesive mass is about 60 gr/sq·m.

At the oven exit, the adhesive layer and the liner are coupled to a layer of polyester fabric longitudinally containing alternated copper filaments and zinc filaments, separated by the same fabric, loaded with silica.

Preferably, the fabric is a fibrous soft fabric of about 100 grams per square meter with 40 grams per square meter in filaments of copper and zinc and with 20 grams per square meter of silica.

The silica is charged by wetting the fabric with a liquid solution containing silica.

Subsequently, the coil obtained is cut into coils with a band of 90 mm.

At this point, on a rotating die-cutting machine the coupled material is die-cut in a rectangular shape of 90 mm per 140 mm, cutting the liner in half, so that it is easy to remove for the user.

Lastly, the cut patch is automatically inserted into a bag.

For the application, simply open the sachet, remove the patch and separate the patch from its protective liner.

The adhesive part of the patch is applied to the skin where you desire that the antalgic action is performed. The patch is replaced every 12 hours until maximum benefit is achieved.

EXAMPLE 2

Preparation of a pharmaceutical patch for the treatment of osteo-muscular pain with DICLOFENAC SODIUM.

40 kg of solvent acrylic adhesive (for example Duro-tak-87-2054 adhesive), 500 g of Sodium Chloride diluted in $H_2O$ in a 1/1 proportion (obtained by shaking for 5 minutes with a special stirrer), 50 g of Diclofenac Sodium diluted in $H_2O$ in a 100/5 proportion (obtained by shaking for 5 minutes with a suitable stirrer) are added at ambient temperature in a container.

This is mixed for 30 minutes at low speed (120 rev/min) with a propeller stirrer until obtaining a uniform mass.

The preparation and coating operations are to be considered as identical to those described in Example 1.

EXAMPLE 3

Preparation of a cosmetic patch for the treatment on wrinkles around the eyes with HYALURONIC ACID.

30 Kg of solvent acrylic adhesive (for example Duro-tak-2353 by National Starch & Chemical) allowing a breathability of 480 gr/sq·m in 24 hours, are added in a container.

The adhesive is introduced in a propeller mixer.

The propeller is rotated at a speed of 60 revolutions per minute and 250 g of Potassium chloride diluted in $H_2O$ in a 1/1 proportion (obtained by shaking for 5 minutes with a specific stirrer), 10 gr of Hyaluronic Acid with a low molecular weight (35000 Dalton) diluted in $H_2O$ in a 100/3 proportion (obtained by shaking for 15 minutes with a specific stirrer) are added.

This is mixed for 30 minutes at a low speed (120 rpm) with a propeller stirrer until a uniform mass is achieved.

The preparation and coating operations are considered as identical to those described in Example 1, the die-cutting providing a half-moon shape adapted to the eye contour, enclosed in a bag containing two shapes (right eye and left eye).

The patch is replaced every 12 hours until the desired results are achieved.

Patch 1 is an element that can be shaped at pleasure, self-generating microcurrents over all its surface and active on every point and, thanks to an adhesive containing electrolytes, it can conduct microcurrents and be easily applied to the skin where necessary.

This patch is advantageously added with polar or bipolar cosmetic, medical or pharmaceutical substances mixed inside the adhesive that can exert their therapeutic activities in the best way, thanks to the microcurrents promoting skin absorption (enhancers).

The adhesive patches with the characteristics described above have surprisingly showed an effectiveness that is greater than any other treatment with similar systems, namely using patches, with or without the insertion of drugs for the treatment of joint and muscle pain.

They have also shown an increased passage through the skin of dermal cosmetic, medical or pharmaceutical substances that could be contained in the adhesive layer, compared to traditional patches and even compared to oral administration forms.

EXAMPLE 4

This is an example of the preparation of a patch for the treatment of cutaneous lesions with hyaluronic acid.

In a fuser heated at 70°, 30 kg of Demineralised water and 6 kg of hydrolysed Polyvinyl alcohol 32 Kilo dalton (PVA98) are introduced and mixed until a uniform mass and transparent mass is obtained.

Hyaluronic acid powder is added and dispersed while stirring and is stirred until obtaining a clear gel without any lumps.

After checking the complete dispersion of the hyaluronic acid, a slow cooling begins by stirring up to 25° C., stirring until homogeneous conditions are obtained. Always stirring, with a peristaltic pump, the mixture obtained is led to flow onto a doctor blade heated at 30° C. and subsequently is filmed at a thickness of 350 micron on a support with a siliconized polyester tape. During the filming phase, a ventilated tunnel oven equipped with four heating stations having the following temperatures respectively: 80/85/100/80° C. is used.

When taken out of the oven, a transparent film is obtained with a thickness of about 150 micron (resulting from the water evaporation) that can be coupled through a compressor roller to the coil of fabric containing filaments of copper and zinc and impregnated with SIO2.

The result is a laminate on which, after eliminating the protective PET support, one side has an electrodynamic fabric and the other side has a transparent and water-soluble film. By wetting with $H_2O$ or another cosmetic solution, the transparent film turns to a slightly adhesive gel, compatible with the damaged dermis, and can be applied effectively and easily onto the lesion.

The film is die-cut using a roller die, in 7×14 cm rectangles.

These rectangles are automatically inserted into a sealed container acting as a dispensing mechanism for the solid compound.

The invention claimed is:

1. A patch able to produce microcurrents, comprising:
a support for electrodes spaced from each other and able to create voltages typical of galvanic piles, the support comprising a moisture-permeable membrane;
connection means between said electrodes;
an adhesive layer applied on one side of said support and able to adhere to the skin; and
a protection liner applied on the adhesive layer,
wherein the connection means are defined by a material avid of moisture impregnating the membrane that captures sweat fluid molecules when in contact with skin, allowing for ion exchange between the electrodes.

2. The patch according to claim 1, wherein the material avid of moisture and impregnating this moisture-permeable membrane is silica of the type consisting of a silicon dioxide polymer.

3. The patch according to claim 1, wherein the moisture-permeable membrane is a fibrous fabric made of a material chosen among polyester, cotton, viscose, or a mixture chosen among the aforementioned polyester, cotton and viscose.

4. The patch according to claim 1, wherein the material has a weight comprised between 60 and 120 grams per square meter, and in that said silica impregnating the fabric has a weight comprised between 15 and 25 grams per square meter.

5. The patch according to claim 1, wherein the electrodes are parallel to each other and placed inside this fabric.

6. The patch according to claim 1, wherein the electrodes are filaments of copper and zinc, and have a width between 1.5 and 2.5 mm, and are spaced from each other by a section included between 1.5 and 2.5 mm.

7. The patch according to claim 1, wherein the adhesive layer contains electrolytes chosen among Calcium Chloride, Magnesium Chloride, Sodium Chloride and Potassium Chloride.

8. The patch according to claim 1, wherein the adhesive layer contains medical or cosmetic or pharmaceutical substances, made up of at least a part of molecules of the polar or bipolar type.

9. The patch according to claim 1, wherein the medical or cosmetic or pharmaceutical substances are selected among Diclofenac Sodium, Hyaluronic Acid, vitamin E, vitamin A, vitamin C.

10. A process for making a patch able to produce microcurrents, the patch comprising a support supporting electrodes spaced from each other and able to create voltages typical of galvanic piles, connection means between said electrodes, an adhesive layer applied on one side of the support and able to adhere to the skin, and a protection liner applied on said adhesive layer, the process comprising:
providing a moisture-permeable fabric;
arranging the electrodes parallel to each other and within the fabric; and
impregnating the moisture-permeable fabric with a silica consisting of a polymer of silicon dioxide $(SiO_2)_n$, said silica thereby forming the connection means in such a way that the connection means, once in contact with the skin, captures sweat fluid molecules, allowing for ion exchange between the electrodes.

* * * * *